(12) United States Patent
Sawada et al.

(10) Patent No.: US 11,452,843 B2
(45) Date of Patent: Sep. 27, 2022

(54) DEVICE AND METHOD FOR INJECTING A BIOMATERIAL INTO BODY TISSUE

(71) Applicant: TERUMO KABUSHIKI KAISHA, Tokyo (JP)

(72) Inventors: Satoshi Sawada, Kanagawa (JP); Naoya Shimada, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 379 days.

(21) Appl. No.: 16/522,442

(22) Filed: Jul. 25, 2019

(65) Prior Publication Data

US 2019/0344048 A1 Nov. 14, 2019

Related U.S. Application Data

(63) Continuation of application No. PCT/JP2018/002902, filed on Jan. 30, 2018.

(30) Foreign Application Priority Data

Jan. 30, 2017 (JP) .............................. JP2017-014344
Jan. 30, 2017 (JP) .............................. JP2017-014348

(51) Int. Cl.
*A61M 25/00* (2006.01)
*A61B 18/14* (2006.01)

(52) U.S. Cl.
CPC .... *A61M 25/0084* (2013.01); *A61M 25/0043* (2013.01); *A61M 2025/0089* (2013.01);
(Continued)

(58) Field of Classification Search
CPC . A61B 18/1492; A61B 18/1497; A61B 34/20; A61B 2034/105; A61B 5/24; A61B 5/25; A61B 5/6848; A61M 25/0084; A61M 2025/0089
See application file for complete search history.

(56) References Cited

U.S. PATENT DOCUMENTS 5,485,849 A * 1/1996 Panescu ................. A61B 5/053
600/374
5,938,694 A * 8/1999 Jaraczewski ........... A61N 1/056
607/122
(Continued)

FOREIGN PATENT DOCUMENTS

JP 7-507470 A 8/1995
JP 2001-087392 A 4/2001
(Continued)

OTHER PUBLICATIONS

International Preliminary Report on Patentability for International Application No. PCT/JP2018/002902, dated Aug. 8, 2019.
(Continued)

*Primary Examiner* — Nathan R Price
*Assistant Examiner* — Courtney B Fredrickson
(74) *Attorney, Agent, or Firm* — Sheridan Ross, PC

(57) ABSTRACT

An injection device is described including a detection unit that includes an electrode that detects electrical characteristics of a biological tissue, a follow-up mechanism that follows motions of the biological tissue, and a puncture unit capable of puncturing the biological tissue. The injection device is configured to administer a predetermined substance to the biological tissue through a hollow portion defined in the puncture unit. A position of the puncture unit is specified based on a position of the electrode. The follow-up mechanism includes a spiral portion spirally extending around the puncture unit, and being stretchable and compressible along an extending direction of the puncture unit. Electrodes are disposed on an annular distal-end projected plane of the spiral portion, as seen from a distal end side of the puncture unit, along a circumferential direction of the puncture unit.

20 Claims, 9 Drawing Sheets

(52) U.S. Cl.
CPC ............ *A61M 2205/0216* (2013.01); *A61M 2205/0233* (2013.01); *A61M 2205/502* (2013.01); *A61M 2205/505* (2013.01); *A61M 2210/125* (2013.01); *A61M 2210/127* (2013.01); *A61M 2230/65* (2013.01)

(56) References Cited

U.S. PATENT DOCUMENTS

| | | |
|---|---|---|
| 7,749,215 B1 | 7/2010 | Ben-Haim et al. |
| 2002/0087058 A1 | 7/2002 | Fuimaono et al. |
| 2005/0090728 A1* | 4/2005 | Mest ................ A61B 5/287 |
| | | 600/373 |
| 2010/0145306 A1 | 6/2010 | Mickley et al. |

FOREIGN PATENT DOCUMENTS

| | | |
|---|---|---|
| JP | 2003-111740 A | 4/2003 |
| JP | 2004-008264 A | 1/2004 |
| JP | 2005-137898 A | 6/2005 |
| JP | 2007-020628 A | 2/2007 |
| WO | WO 93/25263 | 12/1993 |

OTHER PUBLICATIONS

International Search Report for International Application No. PCT/JP2018/002902, dated Mar. 20, 2018.
Written Opinion for International Application No. PCT/JP2018/002902, dated Mar. 20, 2018.

* cited by examiner

DEVICE AND METHOD FOR INJECTING A BIOMATERIAL INTO BODY TISSUE

CROSS REFERENCE TO RELATED APPLICATIONS

The present application is a continuation of and claims benefit to PCT Application No. PCT/JP2018/002902, filed on Jan. 30, 2018, entitled "INJECTION DEVICE AND INJECTION METHOD" which claims priority to Japanese Patent Application No. 2017-014348, filed on Jan. 30, 2017, and Japanese Patent Application No. 2017-014344, filed on Jan. 30, 2017. The entire disclosures of the applications listed above are hereby incorporated herein by reference, in their entirety, for all that they teach and for all purposes.

FIELD

The present disclosure relates to an injection device and an injection method.

BACKGROUND

Nowadays, a treatment such as injecting a biological substance, for example, cells, a biomaterial, or the like into a tissue in anticipation of curative effects is examined for the treatment of a heart failure. In the technique, an instrument such as catheter is used to inject a biological substance or biomaterial into a tissue. In a treatment in which such catheter is used, a position of an infarct area is specified by mapping a biological tissue, for example, the ventricle of the heart three-dimensions (3D) prior to performing an injection technique. Thereafter, cells or other predetermined substances are injected into a desired site, depending on the treatment of a boundary between the infarct area and normal myocardial tissues.

However, if the treatment is performed after the mapping has been done in advance, it is possible to identify a position of the catheter on the 3D mapping, but it is not easy to reliably identify a position of a tissue into which the cells or the like are actually injected. Particularly, if a biological tissue moves such as the heart beating, the problem becomes noticeable. Japanese Patent Application No. JP-A-2005-137898 discloses a technique of performing a treatment while following a biological tissue.

SUMMARY

Technical Problem

The technique disclosed in Japanese Patent Application No. JP-A-2005-137898 has room for improvement in reliably performing a procedure at a treatment position.

An object of the present disclosure is, in light of this problem, to provide an injection device and an injection method by which it is possible to more reliably perform a procedure at a treatment position.

Solution to the Problem

According to one embodiment of the present disclosure, there is provided an injection device including a detection unit that includes an electrode capable of detecting electrical characteristics of a biological tissue, and a follow-up mechanism that follows motions of the biological tissue, and a puncture unit capable of puncturing the biological tissue, and administering a predetermined substance to the biological tissue through a hollow portion defined in the puncture unit, in which a position of the puncture unit is capable of being specified based on a position of the electrode, in which the follow-up mechanism includes a spiral portion spirally extending around the puncture unit, and being stretchable and compressible along an extending direction of the puncture unit, and in which a plurality of the electrodes are disposed on an annular distal-end projected plane of the spiral portion, which is specified when seen from a distal end side of the puncture unit, along a circumferential direction of the puncture unit.

In the injection device according to at least one embodiment of the present disclosure, a distal end of the puncture unit may be disposed offset a distance from a central axis line of the spiral portion.

In the injection device according to at least one embodiment of the present disclosure, the puncture unit may be capable of rotating around the central axis line of the spiral portion, independently of the detection unit.

In the injection device according to at least one embodiment of the present disclosure, the puncture unit may include a sensor disposed at a distal end thereof, which is capable of detecting information associated with the biological tissue.

In the injection device according to at least one embodiment of the present disclosure, the spiral portion may include an annular portion disposed at a distal end thereof, which is annularly formed in a free state, and the electrodes may be provided on a distal surface of the annular portion.

In the injection device according to at least one embodiment of the present disclosure, wherein the follow-up mechanism is a first follow-up mechanism and the puncture unit may include a second follow-up mechanism that follows motions of the biological tissue.

According to one embodiment of the present disclosure, there is provided an injection method executed using an injection device which includes a detection unit including an electrode and a follow-up mechanism that follows motions of a biological tissue, and a puncture unit, in which the follow-up mechanism includes a spiral portion spirally extending around the puncture unit and being stretchable and compressible along an extending direction of the puncture unit, and in which a plurality of the electrodes are disposed on an annular distal-end projected plane of the spiral portion, which is specified when seen from a distal end side of the puncture unit, along a circumferential direction of the puncture unit, the method including a detection step of bringing the electrodes into contact with the biological tissue, and detecting electrical characteristics of the biological tissue, a determination step of determining whether there is an infarct at a puncture position of the puncture unit, based on the detected electrical characteristics, and an administration step of puncturing the biological tissue via the puncture unit, and administering a predetermined substance to the biological tissue through a hollow portion defined in the puncture unit, when it is determined that there is the infarct.

According to one embodiment of the present disclosure, there is provided an injection device including a detection unit that includes an electrode capable of detecting electrical characteristics of a biological tissue, and a first follow-up mechanism that follows motions of the biological tissue, and a puncture unit capable of puncturing the biological tissue, and administering a predetermined substance to the biological tissue through a hollow portion defined in the puncture unit, in which a position of the puncture unit is capable of being specified based on a position of the electrode, in which the puncture unit includes a second follow-up mechanism that follows motions of the biological tissue, in which the first follow-up mechanism includes a linear portion disposed radially outward of the puncture unit, extending along an extending direction of the puncture unit, and being deformable, and in which the electrode is disposed in the linear portion.

In the injection device according to at least one embodiment of the present disclosure, a plurality of the electrodes are disposed in the linear portion, and when a proximal end side of the linear portion rotates around the puncture unit in a state where a distal end of the linear portion is in contact with the biological tissue, the plurality of electrodes are disposed along a circumferential direction of the puncture unit.

In the injection device according to at least one embodiment of the present disclosure, the linear portion may include a flexible portion formed along the circumferential direction of the puncture unit.

The injection device according to at least one embodiment of the present disclosure may include a plurality of the linear portions, in which the plurality of linear portions is provided along a circumferential direction of the puncture unit, and in which the plurality of electrodes is disposed along the circumferential direction of the puncture unit in a state where distal ends of the linear portions are in contact with the biological tissue.

In the injection device according to at least one embodiment of the present disclosure, the linear portion includes a fixing portion at the distal end, which fixes the linear portion to the biological tissue.

In the injection device according to at least one embodiment of the present disclosure, the electrode may be provided at a predetermined position in an extending direction of the linear portion to cover the linear portion along a circumferential direction of the linear portion.

In the injection device according to at least one embodiment of the present disclosure, the second follow-up mechanism follows motions of the biological tissue, independently of the first follow-up mechanism.

According to one embodiment of the present disclosure, there is provided an injection method executed using an injection device which includes a detection unit including an electrode and a first follow-up mechanism that follows motions of a biological tissue, and a puncture unit, in which the puncture unit includes a second follow-up mechanism that follows motions of the biological tissue, in which the first follow-up mechanism includes a linear portion being disposed radially outward of the puncture unit, extending along an extending direction of the puncture unit, and being deformable, and in which the electrode is disposed in the linear portion, the method including a detection step of bringing the electrode into contact with the biological tissue, and detecting electrical characteristics of the biological tissue, a determination step of determining whether there is an infarct at a puncture position of the puncture unit, based on the detected electrical characteristics, and an administration step of puncturing the biological tissue via the puncture unit, and administering a predetermined substance to the biological tissue through a hollow portion defined in the puncture unit, when it is determined that there is the infarct.

Non-Exhaustive Advantages

According to the injection device and the injection method of the present disclosure, it is possible to more reliably perform a procedure at a desirable treatment position.

DETAILED DESCRIPTION

Figure 1:
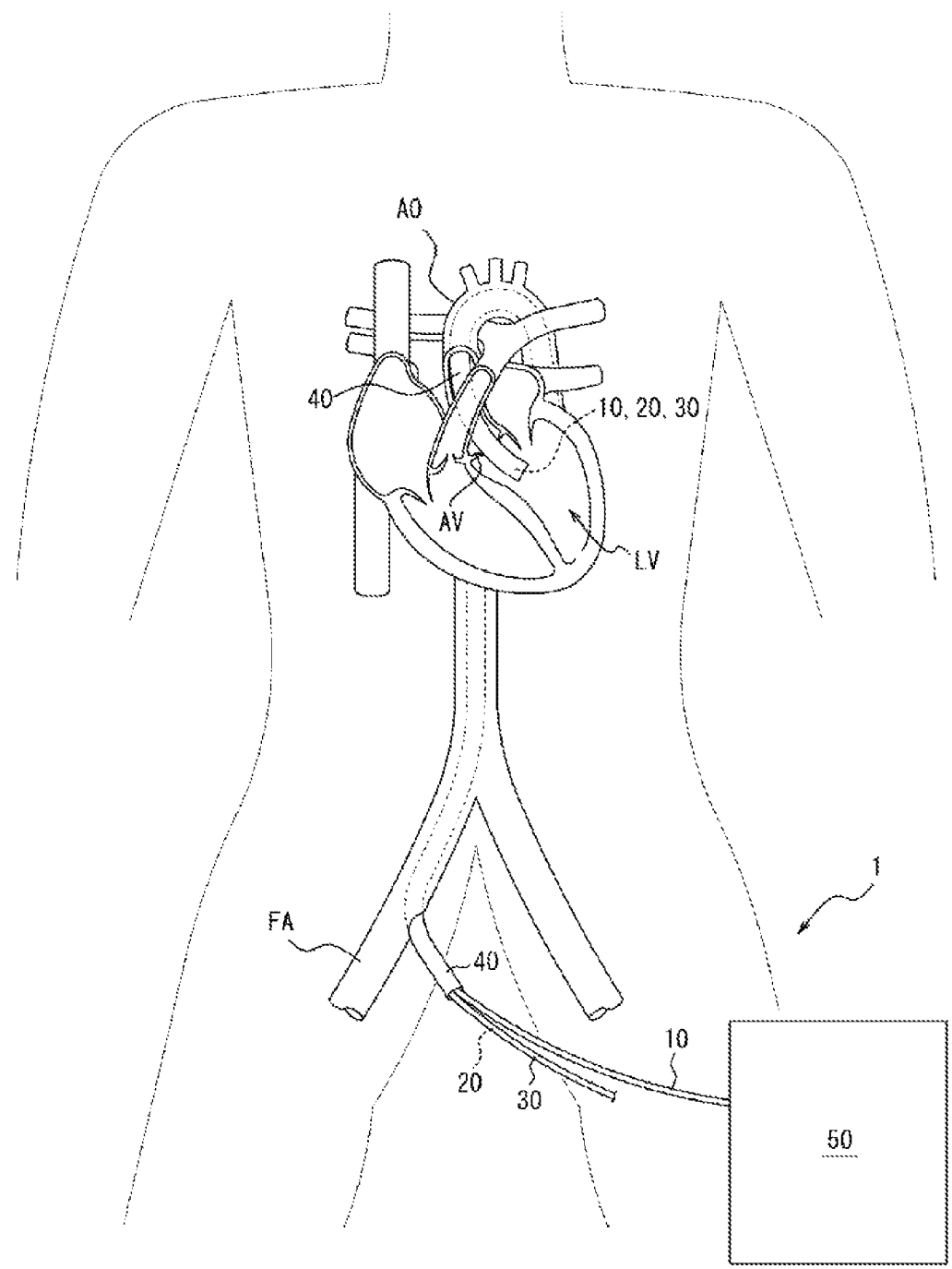
FIG. 1 is a schematic perspective view illustrating an injection device in a body of a patient according to an embodiment of the present disclosure.

Herein, embodiments of the present disclosure will be described with reference to the drawings. The same reference signs will be assigned to the same members in the drawings.

FIG. 1 is a schematic perspective view illustrating an injection device 1 in a body of a patient according to an embodiment of the present disclosure. As illustrated in FIG. 1, the injection device 1 includes a detection unit 10, a puncture unit 20, a catheter 30, an outer cylindrical member 40, or sheath, and a measuring instrument 50. FIG. 1 illustrates a state where the outer cylindrical member 40 extends, via an aorta AO, from a femoral artery FA to an aortic valve AV which is an inlet of a left ventricle LV of a cardiac cavity, and the detection unit 10, the puncture unit 20, and the catheter 30 are delivered to the left ventricle LV through the outer cylindrical member 40. The present disclosure is not limited to a case where the outer cylindrical member 40 extends from the femoral artery FA. The outer cylindrical member 40 may extend to the aortic valve AV, for example, from the radial artery at the wrist, or the like.

Herein, in the injection device 1, a "distal end" and a "proximal end" may refer to a tip and abase of an elongated member, such as the detection unit 10, the puncture unit 20, the catheter 30, and the outer cylindrical member 40, in an insertion direction, respectively, which is inserted into the body of a patient.

Figure 2:
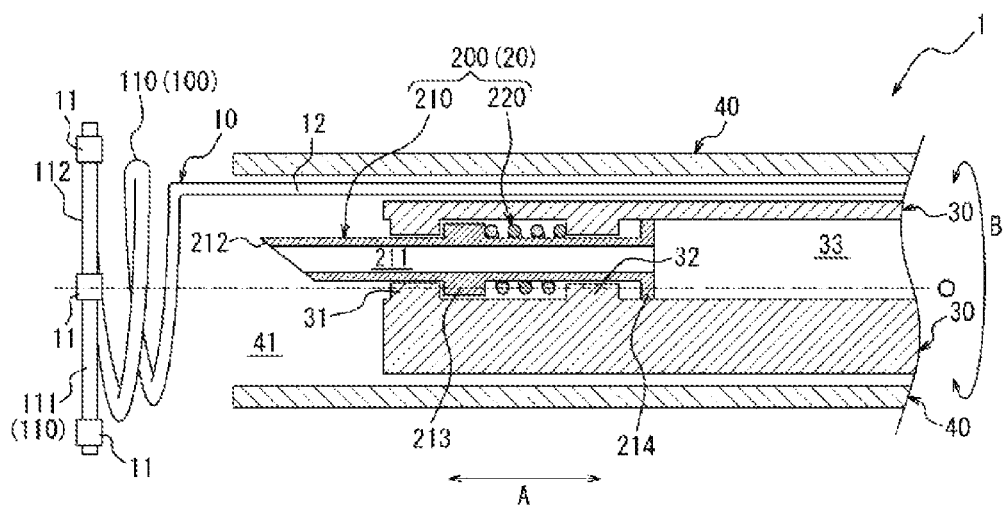
FIG. 2 is a partial cross-sectional plan view illustrating a portion of a distal end of the injection device of FIG. 1.
Figure 3:
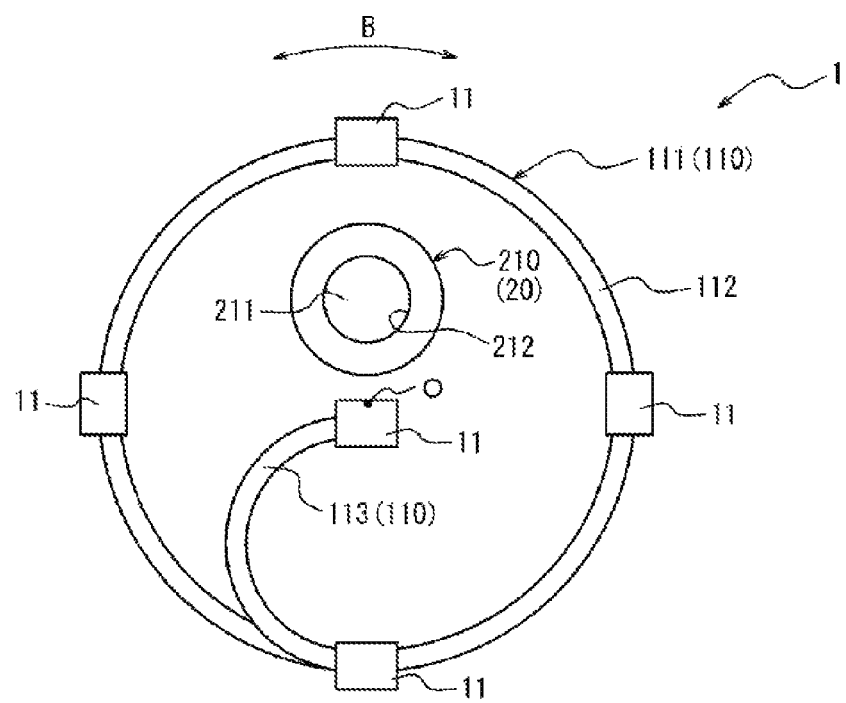
FIG. 3 is a schematic view of the injection device of FIG. 2 as seen from a distal end side thereof.

FIG. 2 is a partial cross-sectional plan view illustrating a portion of a distal end of the injection device 1. FIG. 3 is a schematic view of the injection device 1 as seen from a distal end side thereof. FIGS. 2 and 3 illustrate a state (e.g., a second state, which will be described later) of the injection device 1, in which a spiral portion 110 (described later) of the detection unit 10 is pushed out from a distal end of the outer cylindrical member 40. In FIG. 3, configuration members other than an annular portion 111 (described later) and the puncture unit 20 are not illustrated for the sake of clarity.

As illustrated in FIG. 2, the detection unit 10 includes electrodes 11, a first follow-up mechanism 100 that supports the electrodes 11, and a straight line portion 12 which is substantially linear and connected to a base portion side of the first follow-up mechanism 100. The electrodes 11 are disposed at a tip of the detection unit 10, and are capable of detecting electrical characteristics of a biological tissue with which the electrodes 11 come into contact. The electrical characteristics of the biological tissue detectable by the electrodes 11 may include, but are in no way limited to, a membrane potential of the biological tissue, an impedance between the electrodes 11, and the like. The first follow-up mechanism 100 is a mechanism that follows, or otherwise accommodates, motions of the biological tissue in contact with the electrodes 11. The straight line portion 12 extends inside the outer cylindrical member 40 along an extending direction of the outer cylindrical member 40.

The material of the electrode 11 may comprise electrical conductivity, biocompatibility, and the ease to manufacture. Examples of the material of the electrode may include, but are in no way limited to, metals such as gold, silver, platinum, titanium, stainless steels, and copper, and conductive polymer materials such as PEDOT:PSS. An electric shock in the living body is taken into consideration, and thus portions other than a contact portion in contact with the biological tissue may be covered with an insulator protecting the living body from inadvertent electrical contact, discharge, and/or shock. Examples of the material of the insulator may include, but are in no way limited to, materials having electrical insulating properties such as synthetic non-woven fabrics in addition to resin materials such as synthetic rubbers, ceramics, glass, vinyl chloride, epoxy resins, polyethylene naphthalate films, polyethylene terephthalate films, and polyamideimide films.

As illustrated in FIGS. 2 and 3, the first follow-up mechanism 100 may include a spiral portion 110 that spirally, or helically, extends around the puncture unit 20. The spiral portion 110 is stretchable and compressible along an extending direction A of the puncture unit 20, and thus the spiral portion 110 is capable of flexibly following motions (for example, heart beats) of a biological tissue in contact with the electrodes 11, while maintaining a state of contact with the biological tissue. As illustrated in FIGS. 2 and 3, the spiral portion 110 includes the annular portion 111 at a distal end of the spiral portion 110, which is annularly formed in a free state where the annular portion 111 is pushed out, or otherwise ejected, from the distal end of the outer cylindrical member 40. When delivering the annular portion 111 to a target lesion from outside of the body, it is possible to accommodate the annular portion 111 inside the outer cylindrical member 40 by pulling the annular portion 111 into the outer cylindrical member 40. The electrodes 11 are provided on a distal surface 112 of the annular portion 111. Stated another way, as illustrated in FIG. 3, a plurality of the electrodes 11 may be disposed on an annular distal-end projected plane (that is, the distal surface 112 of the annular portion 111) of the spiral portion 110, which is specified when seen from a distal end side of the puncture unit 20, along a circumferential direction B of the puncture unit 20. In some embodiments, the electrodes 11 may be circularly disposed along the distal surface 112. Two or more electrodes 11 may be disposed along the distal surface 112. Additionally or alternatively, four or five electrodes 11 may be disposed along the distal surface 112.

The puncture unit 20 is capable of puncturing a biological tissue via a distal end thereof, and administering a predetermined substance to the biological tissue through a hollow portion 211, which will be described in detail later. The position of the puncture unit 20 can be specified based on the positions of the electrodes 11. Specifically, a puncture position in a state (e.g., a third state, which will be described later) where the puncture unit 20 punctures the biological tissue can be specified based on the positions of the electrodes 11.

The puncture unit 20 includes a second follow-up mechanism 200 that follows motions of a biological tissue. Independently of the first follow-up mechanism 100, the second follow-up mechanism 200 follows motions of the biological tissue. Stated another way, the second follow-up mechanism 200 follows motions of the biological tissue without connection with the first follow-up mechanism 100 following motions of the biological tissue. The second follow-up mechanism 200 includes a needle member 210 (e.g., a hollow needle, cannula, etc.), and an elastic member 220 (e.g., a compression spring, bellows coupling, etc.) as a biasing member. The hollow portion 211 is defined in the needle member 210. The hollow portion 211 opens at a distal end 212 and a proximal end of the needle member 210. The needle member 210 includes a large-diameter portion 213. A movement of the large-diameter portion 213 in the extending direction A is limited by a distal end-side decreased diameter portion 31, or distal interior flange, and a proximal end-side decreased diameter portion 32, or proximal interior flange, of the catheter 30 which will be described later. The needle member 210 includes a sliding portion 214 at a proximal end, and the sliding portion 214 is capable of sliding in close contact with an inner peripheral surface of a lumen 33 (described later) of the catheter 30.

As illustrated in FIG. 3, the distal end 212 of the puncture unit 20 is disposed offset from a central axis line O of the spiral portion 110. Because the distal end 212 of the puncture unit 20 is disposed offset from the central axis line O, it is possible to rotate also the puncture unit 20 around the central axis line O along the circumferential direction B, and change the puncture position by rotating the outer cylindrical member 40 around the central axis line O of the spiral portion 110 along the circumferential direction B. Independently of the detection unit 10, the puncture unit 20 may be capable of rotating around the central axis line O. Specifically, independently of the detection unit 10 and the outer cylindrical member 40, the puncture unit 20 may be capable of rotating around the central axis line O on a proximal end side. Therefore, it is possible to rotate only the puncture unit 20 without rotating the electrodes 11.

As illustrated in FIG. 3, the spiral portion 110 may include an extending portion 113 that extends radially inward of the annular portion 111. The electrode 11 may be disposed in the extending portion 113. As described above, because the electrode 11 is disposed in the extending portion 113 extending radially inward of the annular portion 111, it is possible to improve the accuracy of specifying the position of the puncture unit 20 based on the positions of the electrodes 11.

As illustrated in FIG. 2, the elastic member 220 is positioned inside the catheter 30. Specifically, the elastic member 220 is disposed between a proximal end of the large-diameter portion 213 of the needle member 210 and a distal end of the proximal end-side decreased diameter portion 32 of the catheter 230. The elastic member 220 biases the needle member 210 to a distal end side with respect to the catheter 30. The elastic member 220 is stretchable and compressible in the extending direction A as the needle member 210 moves in the extending direction A. Therefore, the needle member 210 is capable of following motions of the biological tissue punctured by the distal end 212, and maintaining a puncture state while keeping a puncture depth in the biological tissue constant. In FIG. 2, the elastic member 220 is disposed between the proximal end of the large-diameter portion 213 of the needle member 210 and the distal end of the proximal end-side decreased diameter portion 32 of the catheter 230; however, the present disclosure is not limited to the disposition illustrated. Additionally or alternatively to the disposition illustrated in FIG. 2, for example, the elastic member 220 may be disposed between a distal end of the large-diameter portion 213 of the needle member 210 and a proximal end of the distal end-side decreased diameter portion 31 of the catheter 230. The elastic member 220 is formed of one or more springs or the like.

As illustrated in FIG. 2, the lumen 33 is defined in the catheter 30, and opens at a distal end and a proximal end of the catheter 30. The catheter 30 includes a distal end-side decreased diameter portion 31 and the proximal end-side decreased diameter portion 32 on the inner peripheral surface of the lumen 33. The catheter 30 accommodates the puncture unit 20 in the lumen 33. The lumen 33 communicates with the hollow portion 211, and forms a flow path (e.g., a fluid flow path, etc.) for administering a predetermined substance to a biological tissue.

In one embodiment, a forming material of the catheter 30 may have a certain level of flexibility, and examples of the forming material may include, but are in no way limited to, metal and/or resin. Examples of the metal may include, but are in no way limited to, pseudoelastic alloys (including superelastic alloys) such as Ni—Ti alloys (e.g., Nitinol, etc.), stainless steels (for example, SUS304, SUS303, SUS316, SUS316L, SUS316J1, SUS316J1L, SUS405, SUS430, SUS434, SUS444, SUS429, SUS430F, SUS302, that is, all types of SUS), cobalt-based alloys, precious metals such as gold and platinum, tungsten-based alloys, and carbon-based materials (including piano wire, etc.). Examples of the resin may include, but are in no way limited to, polymer materials such as polyolefin (for example, polyethylene, polypropylene, polybutene, ethylene-propylene copolymer, ethylene-vinyl acetate copolymer, ionomer, or a mixture of two or more thereof), polyvinyl chloride, polyamide, polyamide elastomer, polyester, polyester elastomer, polyurethane, polyurethane elastomer, polyimide, and fluorine resin, a mixture of the polymer materials, or two or more of the above polymer materials. Additionally or alternatively, engineering plastics represented by polyether ether ketone are another example of the forming material of the catheter 30. In some embodiments, the catheter 30 can be formed of a multi-layer tube made from a compound formed of the metals and/or the resins.

As illustrated in FIG. 2, the outer cylindrical member 40 is a cylindrical member including a hollow portion 41 through which the distal end of the outer cylindrical member 40 communicates with a proximal end of the outer cylindrical member 40. The hollow portion 41 accommodates the detection unit 10, the puncture unit 20, and the catheter 30.

Figure 4:
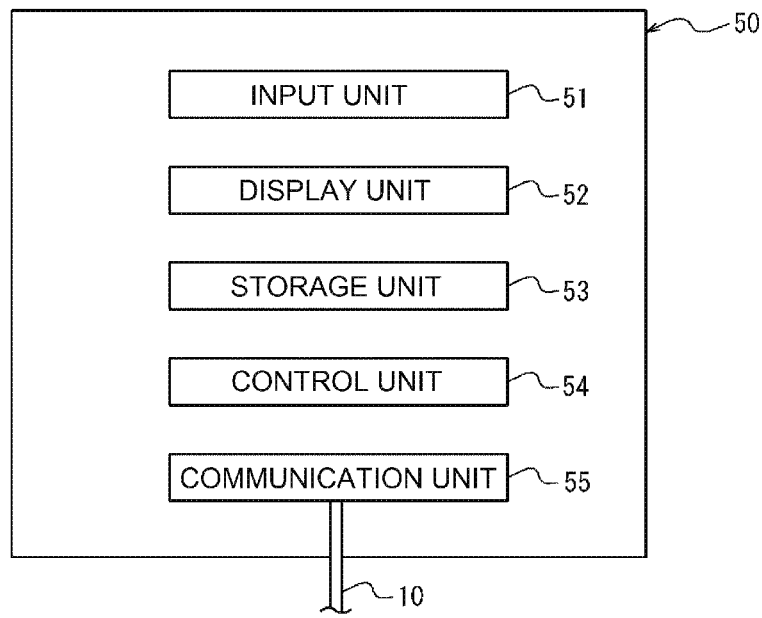
FIG. 4 is a schematic block diagram illustrating a configuration of a measuring instrument of FIG. 1.

FIG. 4 is a schematic block diagram illustrating a configuration of the measuring instrument 50. As illustrated in FIG. 4, the measuring instrument 50 may include an input unit 51, a display unit 52, a storage unit 53, a control unit 54, and a communication unit 55.

The input unit 51 receives an input operation performed by an operator, and outputs received input information to the control unit 54. The input unit 51 is formed of an input device such as keyboard or mouse.

The display unit 52 displays a display screen generated by the control unit 54. The display unit 52 is formed of a display device such as liquid crystal display device, organic EL display device, and/or the like.

The storage unit 53 stores various information and programs for causing the control unit 54 to execute specific functions. The storage unit 53 may store mapping data of a biological tissue such as heart, which is measured in advance by 3D mapping or the like. The storage unit 53 is formed of a storage device, or other computer readable memory device, such as RAM or ROM.

The control unit 54 controls an operation of each configuration part of the measuring instrument 50. The control unit 54 executes a specific function by reading a specific program. The control unit 54 is formed of a processor, a controller, and/or the like.

The communication unit 55 receives electrical characteristics of a biological tissue which are detected by the detection unit 10, and transmits the received electrical characteristics of the biological tissue to the control unit 54. Communication between the communication unit 55 and the detection unit 10 may be done via wired communication or wireless communication. The communication unit may comprise an electrical interface between the detection unit 10 and one or more components of the measuring instrument 50.

Figure 5:
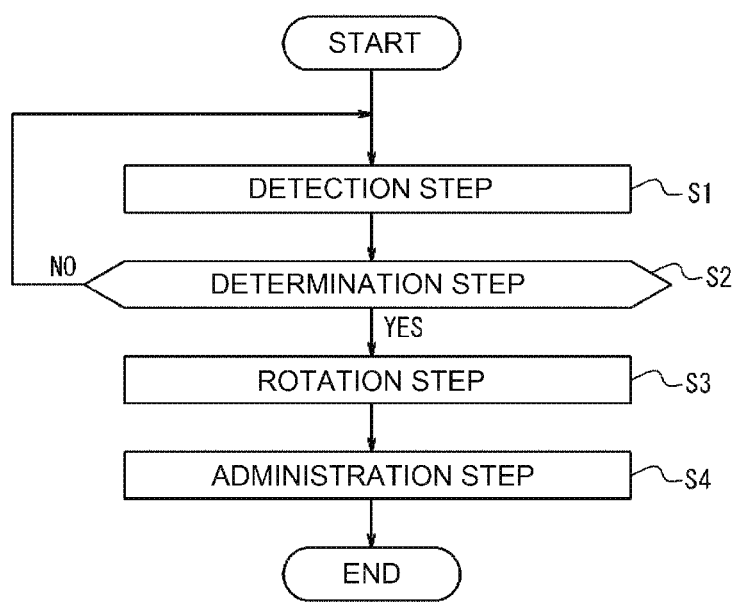
FIG. 5 is a flowchart describing an injection method executed using the injection device of FIG. 1.
Figure 6A:
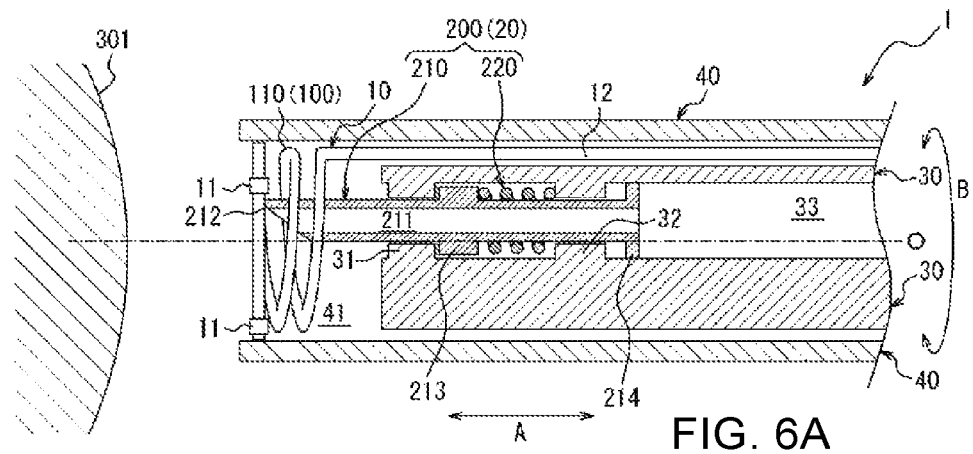
FIG. 6A is a partial cross-sectional plan view of the injection device of FIG. 1 in a first state as the injection method of FIG. 5 is executed.
Figure 6B:
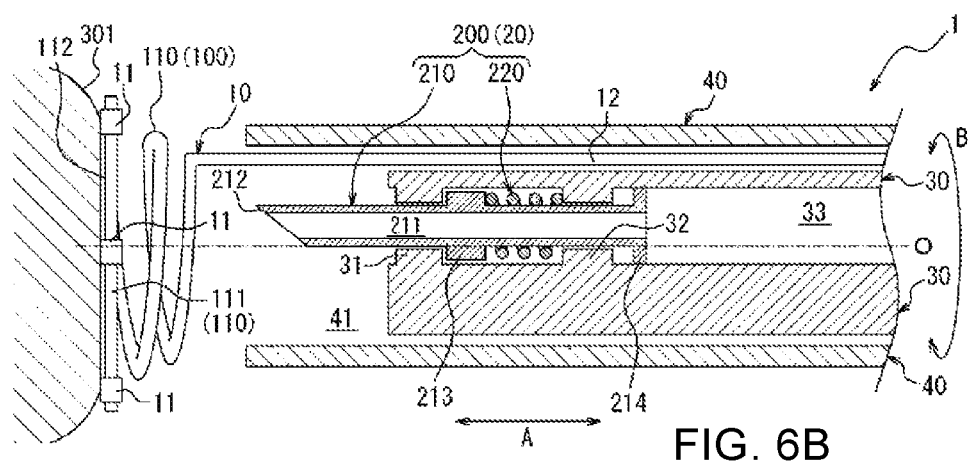
FIG. 6B is a partial cross-sectional plan view of the injection device of FIG. 1 in a second state as the injection method of FIG. 5 is executed.
Figure 6C:
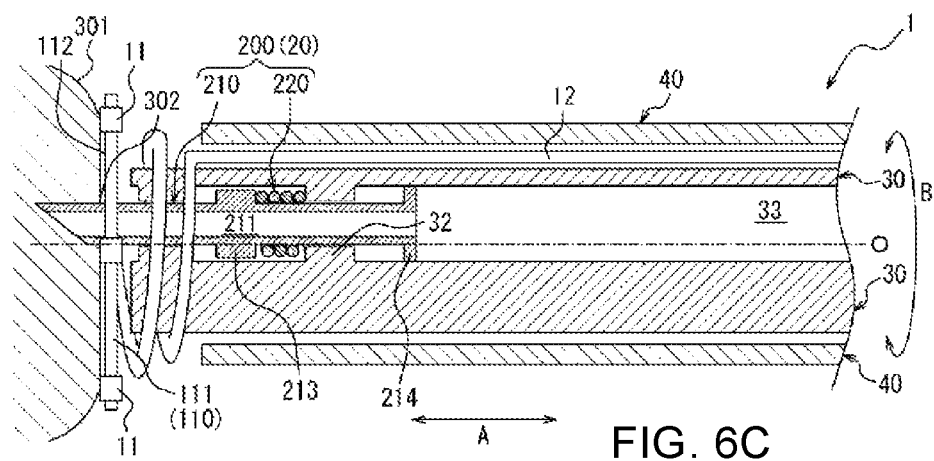
FIG. 6C is a partial cross-sectional plan view of the injection device of FIG. 1 in a third state as the injection method of FIG. 5 is executed.

FIG. 5 is a flowchart describing an injection method executed using the injection device 1. FIGS. 6A-6C illustrate how the state of the injection device 1 changes as the injection method is executed.

As illustrated in FIG. 5, the injection method executed using the injection device 1 includes a detection step S1 of bringing the electrodes 11 into contact with a biological tissue in the body of a subject (e.g., patient, etc.), and detecting electrical characteristic of the biological tissue, a determination step S2 of determining whether there is an infarct at a puncture position 302 of the puncture unit 20, based on the detected electrical characteristics, a rotation step S3 of rotating the puncture unit 20 around the central axis line O of the spiral portion 110 to align the puncture position 302 (refer to FIG. 6C) of the puncture unit 20 with the infarct if it is determined that there is the infarct (determination step S2: YES), prior to administration step S4, which will be described later, and an administration step S4 of puncturing the biological tissue via the puncture unit 20, and administering a predetermined substance to the biological tissue through the hollow portion 211 defined in the puncture unit 20, if it is determined that there is the infarct. If it is determined, in the determination step S2, that there is no infarct (determination step S2: NO), the process returns to the detection step S1, and detection can be repeated again. Herein, each of Steps S1 to S4 will be described in detail.

Firstly, as illustrated in FIG. 6A, the injection device 1 delivers the detection unit 10, the puncture unit 20, and the catheter 30 to the vicinity of a biological tissue through the outer cylindrical member 40 in a state (herein, appropriately referred to as a "first state") where the detection unit 10, the puncture unit 20, and the catheter 30 are accommodated in the hollow portion 41 of the outer cylindrical member 40. In one embodiment, as illustrated in FIG. 1, the detection unit 10, the puncture unit 20, and the catheter 30 are delivered to the left ventricle LV through the outer cylindrical member 40.

Subsequently, as illustrated in FIG. 6B, the spiral portion 110 of the first follow-up mechanism 100 of the detection unit 10 is pushed out, or otherwise ejected, from the inside of the hollow portion 41 of the outer cylindrical member 40. When the spiral portion 110 is pushed out, the electrodes 11 disposed on the distal surface 112 of the annular portion 111 may be placed into contact with an endocardium 301, which is one example of a biological tissue. The electrodes 11 in contact with the endocardium 301 detect electrical characteristics of the endocardium 301 (detection step S1). A state of the injection device 1 at that time may be referred to as the "second state." In the second state, the distal end 212 of the puncture unit 20 does not protrude further to a distal side than the distal end of the spiral portion 110.

Subsequently, the detection unit 10 transmits the electrical characteristics of the endocardium 301, which are detected by the electrodes 11, to the measuring instrument 50 via the communication unit 55. Based on the received electrical characteristics, the control unit 54 determines whether there is an infarct at a puncture position of the puncture unit 20 (determination step S2). In some embodiments, based on the electrical characteristics such as a membrane potential of the biological tissue and an impedance between the electrodes 11, etc., it is possible to determine whether there is an infarct area in the biological tissue. When the storage unit 53 stores mapping data of the biological tissue at that time, which is measured in advance, where there is an infarct can be more accurately determined by the use of the mapping data. Instead of the control unit 54, based on the detected electrical characteristics of the endocardium 301, for example, a user of the injection device 1 may determine whether there is an infarct at the puncture position of the puncture unit 20.

In determination step S2, when the puncture unit 20 rotates around the central axis line O of the spiral portion 110, the control unit 54 may determine whether there is an infarct on a trajectory of the puncture position 302 (refer to FIG. 6C) of the puncture unit 20. If it is determined that there is an infarct (determination step S2: YES), prior to administration step S4, the puncture unit 20 may rotate around the central axis line O of the spiral portion 110 to align the infarct with the puncture position 302 of the puncture unit 20 (rotation step S3). If it is determined that there is no infarct (determination step S2: NO), the process returns to detection step S1, and positions where the electrodes 11 are in contact with the endocardium 301 may be changed.

As illustrated in FIG. 6C, if it is determined that there is an infarct (determination step S2: YES), the puncture unit 20 punctures the endocardium 301, which is a biological tissue. A state of the injection device 1 at that time is referred to as the "third state." Thereafter, a predetermined substance is administered to the endocardium 301 through the hollow portion 211 (administration step S4). As described above, according to the injection method executed using the injection device 1 of the embodiment, it is possible to more reliably perform a procedure at a treatment position. Among other things, the treatment is more reliably performed in that the method and device described herein allow for a precise determination of the location of an infarct relative to a position of the electrodes 11 with flexible attachment. For instance, the puncture unit 20 can be rotated independently of the contacting electrodes 111 to determine an exact location of the infarct. After puncturing, and while administering the predetermined substance, any movement of the biological tissue (e.g., the endocardium 301, etc.) can be accommodated by a corresponding movement of the flexible spiral portion 110 while the puncture unit 20 maintains a substantially constant depth of penetration in the biological tissue via an independently flexible connection.

Figure 7:
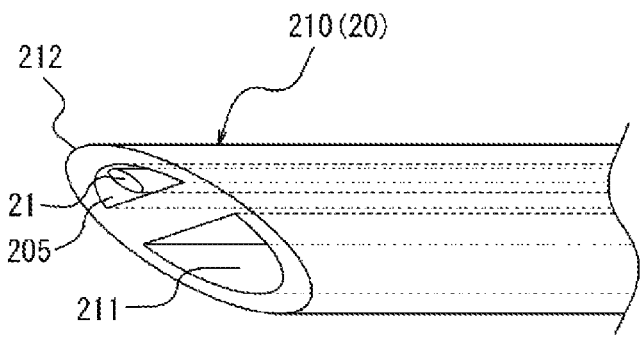
FIG. 7 is a partial view of a puncture unit including a sensor disposed at a distal end thereof in accordance with embodiments of the present disclosure.

FIG. 7 is a partial view of a puncture unit 20 that includes a sensor 21 disposed at the distal end 212. As illustrated in FIG. 7, the needle member 210 of the puncture unit 20 may include the sensor 21 at the distal end 212, which is capable of detecting information on a biological tissue within a sensing range of the sensor 21. The sensor 21 may be a proximity sensor such as a contact sensor that detects contact with the endocardium 301 and/or a motion sensor that detects heart wall motions. FIG. 7 illustrates a configuration in which the sensor 21 may be exposed from the distal end 212 to the outside through a hollow portion 205 for a sensor, which is defined in the puncture unit 20. The present disclosure is not limited to the configuration. For example, the needle member 210 and movements associated with the needle member 210 may function as the sensor 21.

In some embodiments, where the puncture unit 20 includes the sensor 21, the injection method executed using the injection device 1 may further include a re-determination step of re-determining, or confirming, whether there is an infarct at the puncture position 302 of the puncture unit 20, via the sensor 21 prior to administration step S4 if it is determined, in determination step S2, that there is an infarct. Therefore, based at least partially on additional information associated with the biological tissue (e.g., contact, movement, etc.), it is possible to more reliably determine whether there is an infarct at the puncture position 302. As a result, it is possible to more reliably perform a procedure at a treatment position.

Figure 8:
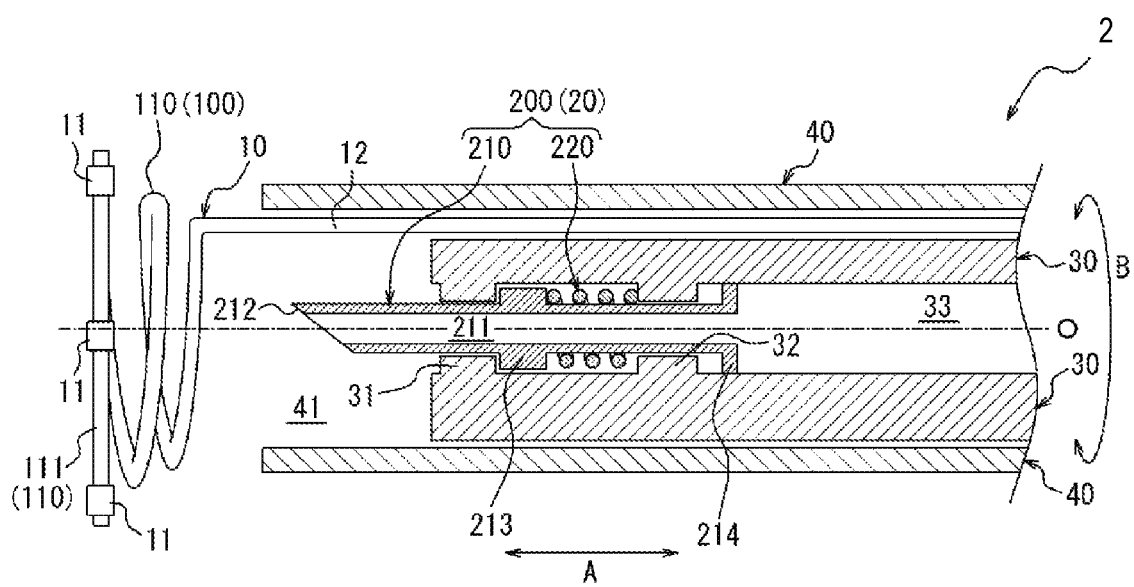
FIG. 8 is a partial cross-sectional plan view illustrating an injection device according to an embodiment of the present disclosure.
Figure 9:
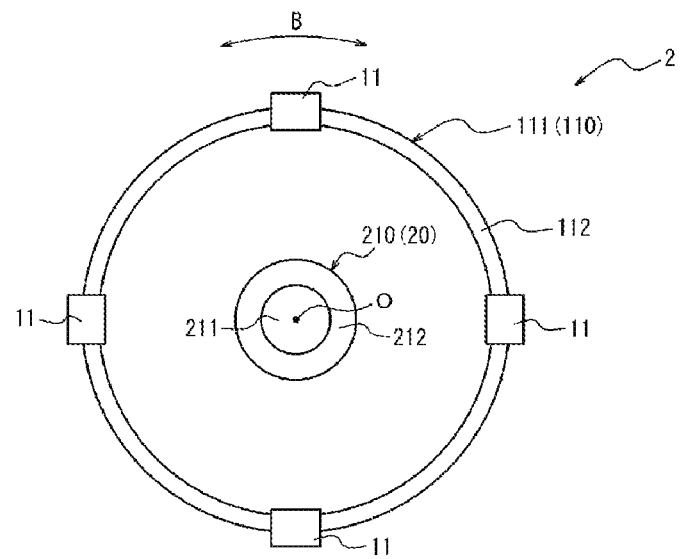
FIG. 9 is a schematic view of the injection device of FIG. 8 as seen from a distal end side thereof.

FIG. 8 is a partial cross-sectional plan view illustrating an injection device 2 according to an embodiment of the present disclosure. FIG. 9 is a schematic view of the injection device 2 as seen from a distal end side thereof.

As illustrated in FIGS. 8 and 9, the injection device 2 may include the detection unit 10, the puncture unit 20, the catheter 30, and the outer cylindrical member 40. In some embodiments, the injection device 3 may include a measuring instrument (not illustrated) that is substantially similar, if not identical, to the measuring instrument 50 described above. In the injection device 2, the distal end 212 of the puncture unit 20 may be disposed on the central axis line O of the spiral portion 110. Because the injection device 2 has the same configuration as that of the injection device 1 except that the distal end 212 of the puncture unit 20 is disposed on the central axis line O of the spiral portion 110, a description of the same configuration members will be omitted. Unlike the injection device 1, in the injection device 2, even though the puncture unit 20 rotates around the central axis line O along the circumferential direction B, it is not possible to change a puncture position relative to the spiral portion, but it is possible to quickly and easily determine the puncture position via the electrodes 11.

Because an injection method executed using the injection device 2 is the same as the injection method executed using the injection device 1, except that rotation step S3 is not included, a description of the injection method will be omitted. As described above, also according to the injection method executed using the injection device 2 of the embodiment, it is possible to more reliably perform a procedure at a treatment position.

Similar to the injection device 1, in the injection device 2, the puncture unit 20 may include the sensor 21 disposed at the distal end 212. When the puncture unit 20 includes the sensor 21, similar to the injection method executed using the injection device 1, the injection method executed using the injection device 2 may further include a re-determination step as previously described.

Figure 10A:
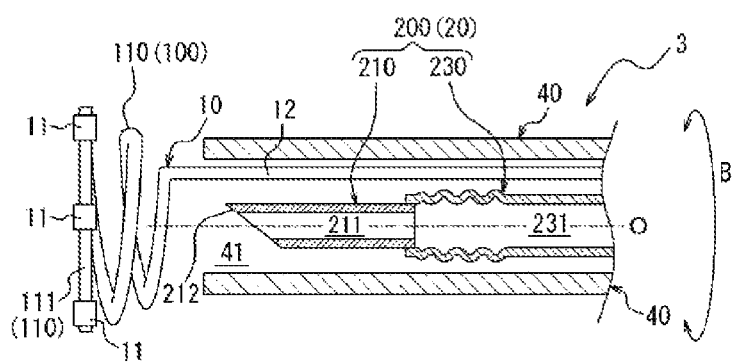
FIG. 10A is a partial cross-sectional plan view of an injection device according to an embodiment of the present disclosure.
Figure 10B:
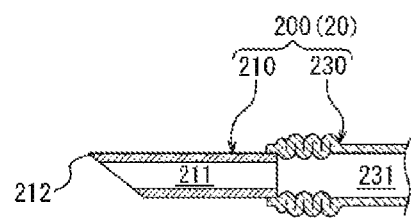
FIG. 10B is a partial cross-sectional plan view of a puncture unit of the injection device of FIG. 10A in a contracted state.

FIGS. 10A-10B illustrate partial cross-sectional views of an injection device 3 and corresponding puncture unit 20, respectively, according to an embodiment of the present disclosure. FIG. 10A illustrates a state where a catheter 230 (described later) is stretched, or expanded along an axial length thereof, and FIG. 10B illustrates a state where the catheter 230 is contracted (e.g., along the axial length). FIG. 10B illustrates only the puncture unit 20 for the sake of clarity in highlighting the contracted state, and flexible end, of the catheter 230 connected with the needle member 210. As illustrated in FIG. 10A, the injection device 3 may include the detection unit 10, the puncture unit 20, and the outer cylindrical member 40. In some embodiments, the injection device 3 may include a measuring instrument (not illustrated) that is substantially similar, if not identical, to the measuring instrument 50 described above. As illustrated in FIG. 10A, in the injection device 3, the second follow-up mechanism 200 includes the needle member 210, and the catheter 230 as a biasing member. Unlike the injection device 1, the injection device 3 does not include the catheter 30. Because the injection device 3 has the same configuration as that of the injection device 1, except for the foregoing configuration, a description of the same configuration members will be omitted.

A lumen 231 is defined in the catheter 230, and opens at a distal end and a proximal end of the catheter 230. The catheter 230 holds the needle member 210 inside the lumen 231 in a state where the distal end 212 of the needle member 210 is exposed to the outside. The lumen 231 communicates with the hollow portion 211 of the needle member 210, and forms a flow path for administering a predetermined substance to a biological tissue. The catheter 230 has a bellows-shaped outer surface, and is stretchable and compressible along an extending direction of the catheter 230.

Because an injection method executed using the injection device 3 is the same as the injection method executed using the injection device 1, except that rotation step S3 is not included, a description of the injection method will be omitted. As described above, also according to the injection method executed using the injection device 3 of the embodiment, it is possible to more reliably perform a procedure at a treatment position.

Similar to the injection device 1, in the injection device 3, the puncture unit 20 may include the sensor 21 disposed at the distal end 212. When the puncture unit 20 includes the sensor 21, similar to the injection method executed using the injection device 1, the injection method executed using the injection device 3 may further include a re-determination step as previously described.

Figure 11:
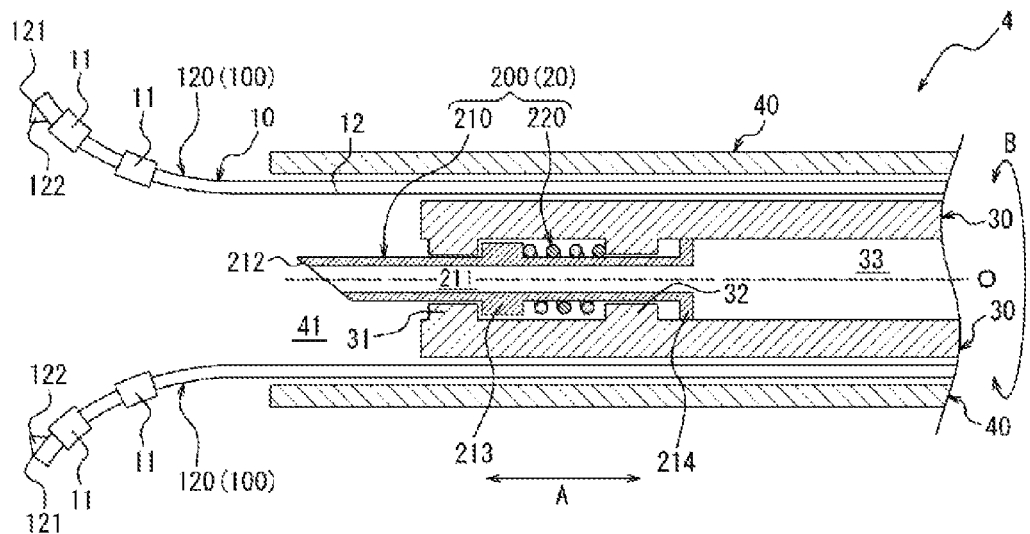
FIG. 11 is a partial cross-sectional plan view illustrating a portion of a distal end of an injection device according to an embodiment of the present disclosure.
Figure 12:
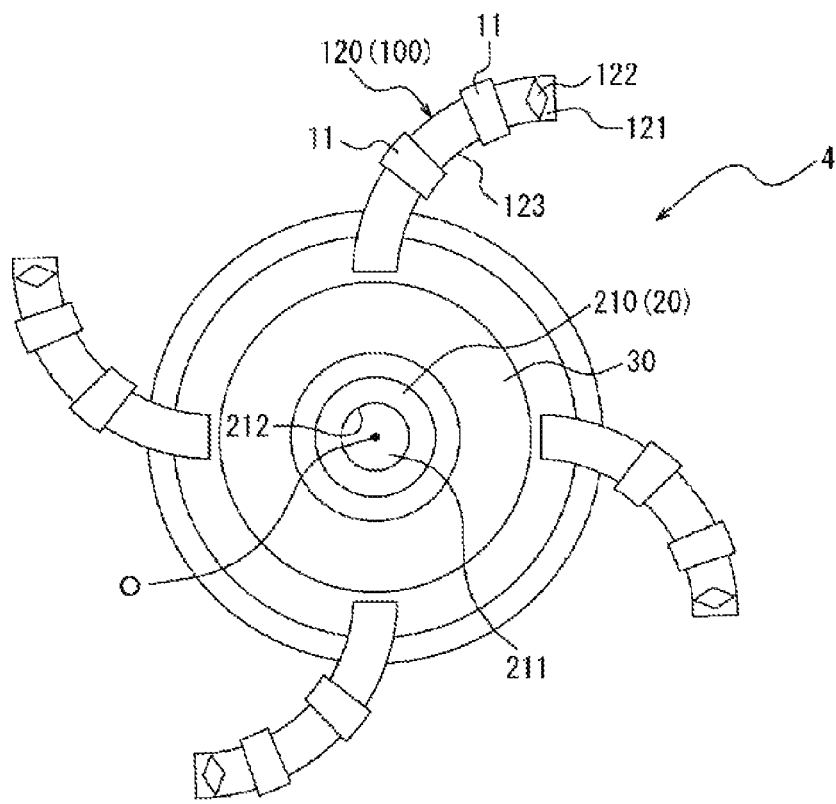
FIG. 12 is a schematic view of the injection device of FIG. 11 as seen from a distal end side thereof.

FIG. 11 is a partial cross-sectional plan view illustrating a portion of a distal end of an injection device 4 according to an embodiment of the present disclosure. FIG. 12 is a schematic view of the injection device 4 as seen from a distal end side thereof.

As illustrated in FIG. 11, the injection device 4 may include the detection unit 10, the puncture unit 20, the catheter 30, and the outer cylindrical member 40. In some embodiments, the injection device 4 may include a measuring instrument (not illustrated) that is substantially similar, if not identical, to the measuring instrument 50 described above. Because the injection device 4 has the same configuration as that of the injection device 2 of the second embodiment of the present disclosure, except for the detection unit 10, a description of the same configuration members will be omitted.

As illustrated in FIG. 11, the detection unit 10 includes the electrodes 11, the first follow-up mechanism 100, and the straight line portion 12 which is connected to the base portion side of the first follow-up mechanism 100. The electrodes 11 are disposed at a tip of the detection unit 10, and are capable of detecting electrical characteristics of a biological tissue with which the electrodes 11 come into contact. The first follow-up mechanism 100 is a mechanism that follows motions of the biological tissue in contact with the electrodes 11. The straight line portion 12 extends inside the outer cylindrical member 40 along the extending direction of the outer cylindrical member 40.

As illustrated in FIGS. 11 and 12, the first follow-up mechanism 100 may include a plurality of flexible linear portions 120 which are disposed radially outward of the puncture unit 20 and extend along the extending direction A of the puncture unit 20. The linear portion 120 is formed of a flexible member, which can be bent, twisted, or otherwise deformed. In the example illustrated in FIGS. 11 and 12, each of the linear portions 120 is curved such that a distal end 121 is positioned radially outward of the puncture unit 20. The electrode 11 is provided at a predetermined position in an extending direction of the linear portion 120 to cover the linear portion 120 along a circumferential direction of the linear portion 120. The linear portion 120 includes a fixing portion 122 at the distal end 121, which fixes the linear portion 120 to a biological tissue. The fixing portion 122 is formed of, for example, a claw-shaped member, and is a member that fixes the distal end 121 of the linear portion 120 to a biological tissue at a contact position when coming into contact with the biological tissue. The fixing portion 122 may be formed by the electrode 11. In the example illustrated in FIG. 11, the plurality of electrodes 11 are disposed in each of the linear portions 120, and one or more electrodes 11 may be disposed in, or along a length of, each of the linear portions 120.

Figure 13A:
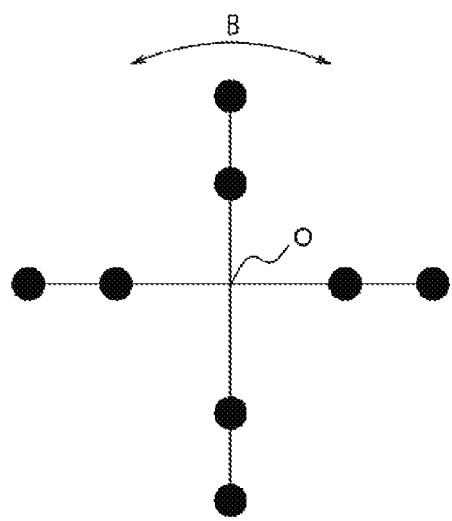
FIG. 13A is a schematic diagram of an example of the disposition of electrodes of the injection device of FIG. 11, which come into contact with a biological tissue in a first state.
Figure 13B:
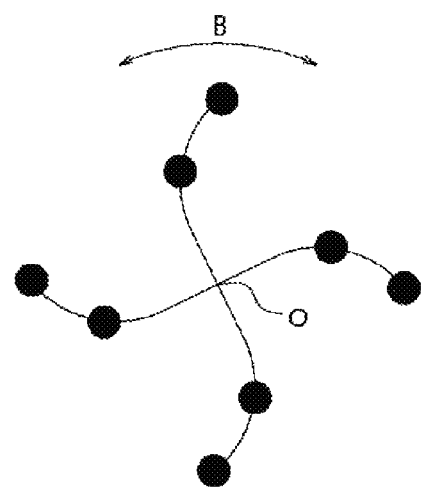
FIG. 13B is a schematic diagram of an example of the disposition of electrodes of the injection device of FIG. 11, which come into contact with a biological tissue in a second, rotated, state.

FIGS. 13A-13B are schematic diagrams of examples of the disposition of the electrodes 11 of the injection device 4, which come into contact with a biological tissue. In FIGS. 13A-13B, each filled black circle indicates a position where the electrode 11 may be disposed. Because the plurality of linear portions 120 are provided along the circumferential direction B of the puncture unit 20 as illustrated in FIG. 12, the plurality of electrodes 11 are disposed along the circumferential direction B of the puncture unit 20 as illustrated in FIG. 13A, in a state where the distal ends 121 of the linear portions 120 are in contact with the biological tissue.

Proximal end sides of the linear portions 120 may rotate around the puncture unit 20 along the circumferential direction B while the distal ends 121 are being fixed to the biological tissue via the fixing portions 122 in a state where the distal ends 121 of the linear portions 120 are in contact with the biological tissue. Therefore, as illustrated in FIG. 13B, the plurality of electrodes 11 are more widely disposed along the circumferential direction B of the puncture unit 20. As a result, the electrodes 11 are capable of acquiring electrical characteristics of a wider range of the biological tissue. As illustrated in FIG. 12, the linear portion 120 may have a flexible portion 123 formed along the circumferential direction B of the puncture unit 20. As a result, it becomes easier to dispose the electrodes 11 as illustrated in FIG. 13B.

Figure 14:
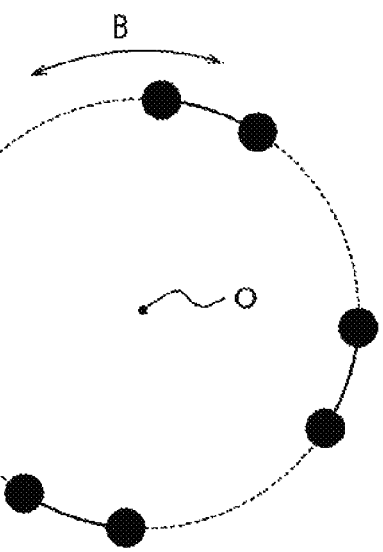
FIG. 14 is a schematic diagram of an example of the disposition of the electrodes of the injection device of FIG. 11, which come into contact with the biological tissue along a length of a circumferential circle.

FIG. 14 is a schematic diagram (of an example of the disposition of the electrodes 11 of the injection device 4, which come into contact with a biological tissue along a length of a circumferential circle. In FIG. 14, each filled black circle indicates a position where the electrode 11 may be disposed. When the linear portions 120 are not curved such that the distal ends 121 are not positioned radially outward of the puncture unit 20, as illustrated in FIG. 14, it is possible to dispose the electrodes 11 on the same circle along the circumferential direction B of the puncture unit 20 by rotating the proximal end sides of the linear portions 120 around the puncture unit 20 along the circumferential direction B while fixing the distal ends 121 of the linear portions 120 to the biological tissue.

Figure 15A:
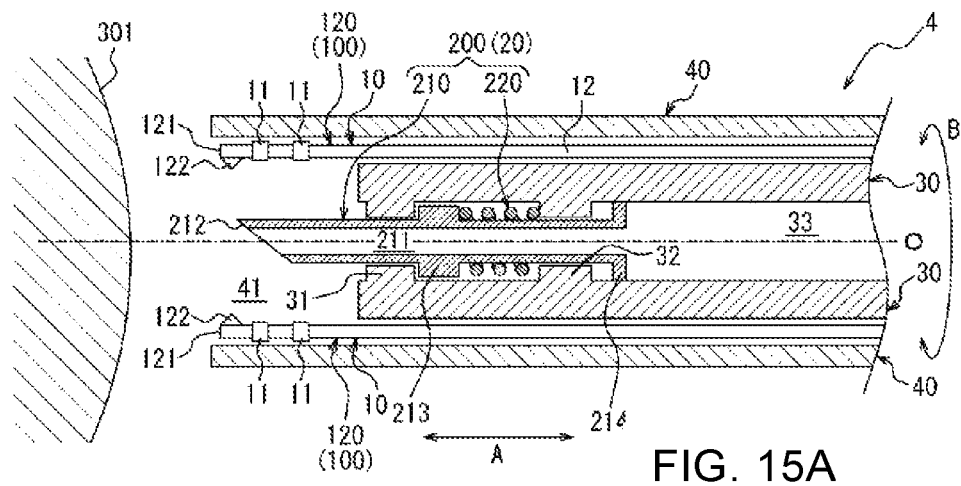
FIG. 15A is a partial cross-sectional plan view of a first state of the injection device of FIG. 11 as an injection method is executed using the injection device of FIG. 11.
Figure 15B:
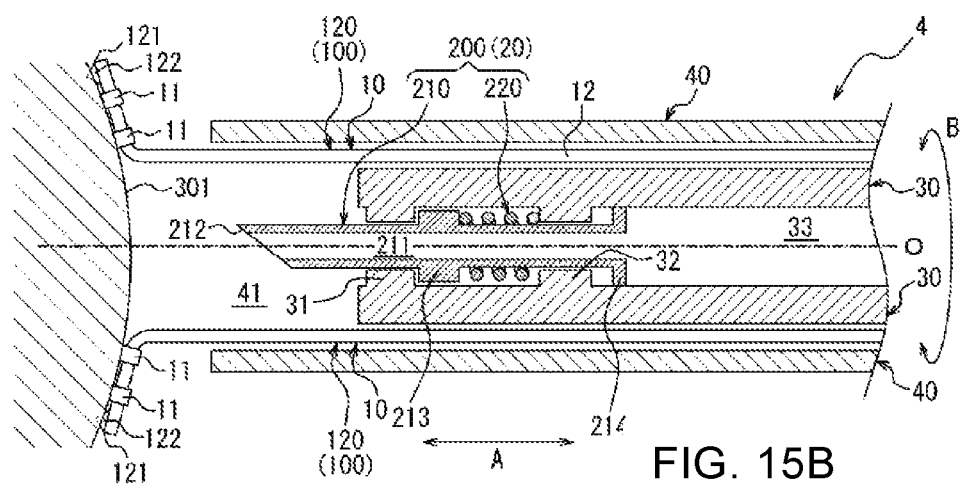
FIG. 15B is a partial cross-sectional plan view of a second state of the injection device of FIG. 11 as the injection method is executed using the injection device of FIG. 11.
Figure 15C:
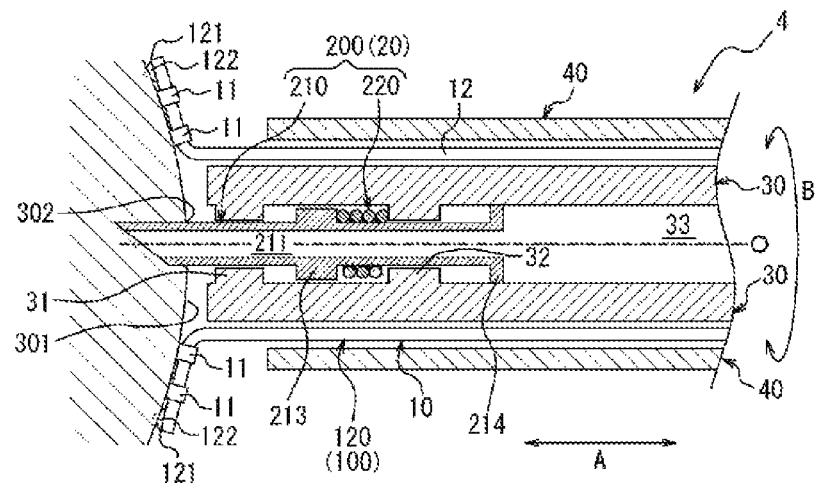
FIG. 15C is a partial cross-sectional plan view of a third state of the injection device of FIG. 11 as the injection method is executed using the injection device of FIG. 11.

FIGS. 15A-15C are partial cross-sectional plan views of states of the injection device 4 as an injection method is executed using the injection device 4. Except that rotation step S3 is not included, the injection method executed using the injection device 4 is the same as the injection method executed using the injection device 1 previously described. That is, the injection method executed using the injection device 4 includes a detection step S1, a determination step S2, and an administration step S4. Herein, points of difference between the injection method executed using the injection device 4 and the injection method executed using the injection device 1 will be described.

Firstly, as illustrated in FIG. 15A, the injection device 4 delivers the detection unit 10, the puncture unit 20, and the catheter 30 to the vicinity of a biological tissue through the outer cylindrical member 40 in the first state where the detection unit 10, the puncture unit 20, and the catheter 30 are accommodated in the hollow portion 41 of the outer cylindrical member 40. In one embodiment, similar to the embodiment described in conjunction with FIG. 1, the detection unit 10, the puncture unit 20, and the catheter 30 are delivered to the left ventricle LV through the outer cylindrical member 40.

Subsequently, as illustrated in FIG. 15B, the linear portions 120 of the first follow-up mechanism 100 of the detection unit 10 are pushed out, or otherwise ejected, from the inside of the hollow portion 41 of the outer cylindrical member 40. When the linear portions 120 are pushed out, the electrodes 11 disposed in the linear portions 120 come into contact with the endocardium 301, which is an example of a biological tissue in accordance with embodiments of the present disclosure. The electrodes 11, which have come into contact with the endocardium 301, detect electrical characteristics of the endocardium 301 (detection step S1). A state of the injection device 4 at that time may be referred to as the "second state." In the second state, the distal end 212 of the puncture unit 20 does not protrude further to the distal side than the distal ends 121 of the linear portions 120.

The injection method executed using the injection device 4 may further include a disposition step of rotating the proximal end sides of the linear portions 120 around the puncture unit 20 along the circumferential direction B, and disposing the plurality of electrodes 11 along the circumferential direction B of the puncture unit 20, prior to detection step S1, in a state where the distal ends 121 of the linear portions 120 are in contact with the biological tissue.

Subsequently, the detection unit 10 transmits the electrical characteristics of the endocardium 301, which are detected by the electrodes 11, to the measuring instrument 50 via the communication unit 55. The control unit 54 determines whether there is an infarct at a puncture position of the puncture unit 20, based on the received electrical characteristics (determination step S2). Determination step S2 is executed in the same way as in the injection method executed using the injection device 1.

As illustrated in FIG. 15C, if it is determined that there is an infarct (determination step S2: YES), the puncture unit 20 punctures the endocardium 301 which is a biological tissue. A state of the injection device 4 at that time may be referred to as the "third state." Thereafter, a predetermined substance is administered to the endocardium 301 through the hollow portion 211 (administration step S4). As described above, also according to the injection method executed using the injection device 4 of the embodiment, it is possible to more reliably perform a procedure at a treatment position. If it is determined that there is no infarct (determination step S2: NO), the process returns to detection step S1, and the positions where the electrodes 11 are in contact with the endocardium 301 may be changed.

Similar to the injection device 1, in the injection device 4, the puncture unit 20 may include the sensor 21 at the distal end 212. When the puncture unit 20 includes the sensor 21, similar to the injection method executed using the injection device 1, the injection method executed using the injection device 4 may further include a re-determination step as previously described.

Similar to the injection device 3, in the injection device 4, the second follow-up mechanism 200 may include the needle member 210, and the catheter 230 as a biasing member. In this case, the injection device 4 may not include the catheter 30.

The present disclosure is not limited to the configuration specified in each of the embodiments, and various modifications can be made without departing from the concept described in the claims.

DESCRIPTION OF REFERENCE CHARACTERS 1, 2, 3, 4 injection device
10 detection unit
11 electrode
12 straight line portion
100 first follow-up mechanism
110 spiral portion
111 annular portion
112 distal surface of annular portion
113 extending portion
120 linear portion
121 distal end of linear portion
122 fixing portion 123 flexible portion
20 puncture unit
21 sensor
200 second follow-up mechanism
205 hollow portion for sensor
210 needle member
211 hollow portion
212 distal end of needle member (puncture unit)
213 large-diameter portion
214 sliding portion
220 elastic member (biasing member)
230 catheter (biasing member)
231 lumen
30 catheter
31 distal end-side decreased diameter portion
32 proximal end-side decreased diameter portion
33 lumen
40 outer cylindrical member
41 hollow portion
50 measuring instrument
51 input unit
52 display unit
53 storage unit
54 control unit
55 communication unit
301 endocardium (biological tissue)
302 puncture position
A extending direction of puncture unit (needle member)
B circumferential direction of puncture unit
O central axis line of spiral portion
AO aorta
AV aortic valve
FA femoral artery
LV left ventricle

What is claimed is:

1. An injection device comprising:
a detection unit that includes an electrode capable of detecting electrical characteristics of a biological tissue, and a follow-up mechanism comprising an elastic member that follows motions of the biological tissue; and
a puncture unit comprising a needle that is capable of puncturing the biological tissue, and administering a predetermined substance to the biological tissue through a hollow portion defined in the needle,
wherein a position of the puncture unit is capable of being specified based on a position of the electrode,
wherein the elastic member of the follow-up mechanism comprises a spiral portion spirally extending around the puncture unit and terminating at a spiral portion end disposed adjacent a central axis line of the spiral portion, the spiral portion, being stretchable and compressible along an extending direction of the puncture unit, and
wherein the electrode comprises a plurality of electrodes that are disposed on an annular distal-end projected plane of the spiral portion, which is specified when seen from a distal end side of the puncture unit, along a circumferential direction of the puncture unit.

2. The injection device according to claim 1, wherein a distal end of the puncture unit is disposed offset a distance from the central axis line of the spiral portion.

3. The injection device according to claim 1, wherein the puncture unit includes a sensor disposed at a distal end thereof, which is capable of detecting information associated with the biological tissue.

4. The injection device according to claim 1, wherein the spiral portion includes an annular portion disposed at a distal end thereof, which is annularly formed in a free state, and wherein each electrode of the plurality of electrodes is provided on a distal surface of the annular portion in the annular distal-end projected plane of the spiral portion.

5. The injection device according to claim 1, wherein the follow-up mechanism is a first follow-up mechanism and the puncture unit includes a second follow-up mechanism comprising a second elastic member that follows motions of the biological tissue.

6. The injection device according to claim 5, further comprising:
a sheath configured to insert into an artery of a body of a subject; and
a catheter disposed within the sheath, wherein the catheter is movable relative to the sheath, and wherein the catheter houses a portion of the puncture unit.

7. The injection device according to claim 6, wherein the second elastic member of the second follow-up mechanism comprises a compression spring disposed between a portion of the puncture unit and the catheter, and wherein the compression spring biases the puncture unit in a position extending distally from a distal end of the catheter toward a direction of the biological tissue.

8. The injection device according to claim 7, wherein the needle comprises a lumen running therethrough, and wherein a fluid flow path is formed through the lumen of the needle and a lumen of the catheter.

9. An injection device comprising:
a detection unit that includes an electrode capable of detecting electrical characteristics of a biological tissue, and a follow-up mechanism comprising an elastic member that follows motions of the biological tissue; and
a puncture unit comprising a needle that is capable of puncturing the biological tissue, and administering a predetermined substance to the biological tissue through a hollow portion defined in the needle,
wherein a position of the puncture unit is capable of being specified based on a position of the electrode,
wherein the elastic member of the follow-up mechanism comprises a spiral portion spirally extending around the puncture unit, and being stretchable and compressible along an extending direction of the puncture unit,
wherein a distal end of the puncture unit is disposed offset a distance from a central axis line of the spiral portion, and
wherein the puncture unit is capable of rotating around the central axis line of the spiral portion, independently of the detection unit, and
wherein the electrode comprises a plurality of electrodes that are disposed on an annular distal-end projected plane of the spiral portion, which is specified when seen from a distal end side of the puncture unit, along a circumferential direction of the puncture unit.

10. The injection device according to claim 9, wherein the puncture unit includes a sensor disposed at a distal end thereof, which is capable of detecting information associated with the biological tissue.

11. The injection device according to claim 9, wherein the spiral portion includes an annular portion disposed at a distal end thereof, which is annularly formed in a free state, and wherein each electrode of the plurality of electrodes is provided on a distal surface of the annular portion in the annular distal-end projected plane of the spiral portion.

12. The injection device according to claim 9, wherein the follow-up mechanism is a first follow-up mechanism and the puncture unit includes a second follow-up mechanism comprising a second elastic member that follows motions of the biological tissue.

13. The injection device according to claim 12, further comprising:
   a sheath configured to insert into an artery of a body of a subject; and
   a catheter disposed within the sheath, wherein the catheter is movable relative to the sheath, and wherein the catheter houses a portion of the puncture unit.

14. The injection device according to claim 13, wherein the second elastic member of the second follow-up mechanism comprises a compression spring disposed between a portion of the puncture unit and the catheter, and wherein the compression spring biases the puncture unit in a position extending distally from a distal end of the catheter toward a direction of the biological tissue.

15. The injection device according to claim 14, wherein the needle comprises a lumen running therethrough, and wherein a fluid flow path is formed through the lumen of the needle and a lumen of the catheter.

16. The injection device according to claim 9, wherein the spiral portion terminates at a spiral portion end disposed adjacent the central axis line of the spiral portion inside an annular portion disposed at a distal end of the spiral portion.

17. An injection method executed using an injection device which includes a detection unit including an electrode and a follow-up mechanism comprising an elastic member that follows motions of a biological tissue, and a puncture unit comprising a needle, in which the elastic member of the follow-up mechanism comprises a spiral portion spirally extending around the puncture unit and being stretchable and compressible along an extending direction of the puncture unit, and in which the electrode comprises a plurality of electrodes that are disposed on an annular distal-end projected plane of the spiral portion, which is specified when seen from a distal end side of the puncture unit, along a circumferential direction of the puncture unit, wherein a distal end of the puncture unit is disposed offset a distance from a central axis line of the spiral portion, and wherein the puncture unit is capable of rotating around the central axis line of the spiral portion, independently of the detection unit, the method comprising:
   a detection step of bringing the electrodes into contact with the biological tissue, and detecting electrical characteristics of the biological tissue;
   a determination step of determining whether there is an infarct at a puncture position of the puncture unit, based on the detected electrical characteristics; and
   an administration step of puncturing the biological tissue via the puncture unit, and administering a predetermined substance to the biological tissue through a hollow portion defined in the puncture unit, when it is determined that there is the infarct.

18. The injection method according to claim 17, wherein prior to the detection step, the method further comprises:
   a delivery step of delivering the detection unit to a vicinity of the biological tissue via a sheath inserted into a body of a subject.

19. The injection method according to claim 18, wherein the determination step further comprises:
   rotating the puncture unit disposed inside the sheath independent of the spiral portion; and
   aligning the puncture position of the puncture unit with the infarct.

20. The injection method according to claim 19, wherein the puncture unit includes a sensor, and wherein the determination step further comprises:
   determining, based on information associated with the biological tissue detected by the sensor, that the infarct is at the puncture position of the puncture unit.

\* \* \* \* \*